US008557269B2

(12) United States Patent
Kleinwaechter et al.

(10) Patent No.: US 8,557,269 B2
(45) Date of Patent: *Oct. 15, 2013

(54) PAPER TISSUE WITH HIGH LOTION TRANSFERABILITY

(75) Inventors: Joerg Kleinwaechter, Hofheim Am Tanus (DE); Dirk Butz, Hofheim Am Tanus (DE); Curtis Allen Marcott, Cincinnati, OH (US); Luigi Di Girolamo, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 1958 days.

This patent is subject to a terminal disclaimer.

(21) Appl. No.: 11/105,996

(22) Filed: Apr. 14, 2005

(65) Prior Publication Data
US 2005/0238700 A1 Oct. 27, 2005

Related U.S. Application Data

(60) Provisional application No. 60/565,105, filed on Apr. 23, 2004.

(51) Int. Cl.
*A61K 9/70* (2006.01)
*D21H 19/66* (2006.01)

(52) U.S. Cl.
USPC .......... 424/414; 424/400; 424/402; 424/443; 162/109; 162/135; 162/158; 162/179

(58) Field of Classification Search
None
See application file for complete search history.

(56) References Cited

U.S. PATENT DOCUMENTS

| 3,994,771 | A | | 11/1976 | Morgan, Jr. et al. |
| 4,300,981 | A | | 11/1981 | Carstens |
| 4,338,876 | A | | 7/1982 | Norton |
| 5,407,665 | A | * | 4/1995 | McLaughlin et al. .......... 424/58 |
| 5,525,345 | A | * | 6/1996 | Warner et al. ................. 424/402 |

(Continued)

FOREIGN PATENT DOCUMENTS

| WO | WO 98/29605 A1 | 7/1998 |
| WO | WO 02/066740 A1 | 8/2002 |

OTHER PUBLICATIONS

Lubrication Engineering: "Sefose (SM), the innovative molecule from P&G Chemicals", (accessed at http://findarticles.com/p/articles/mi_qa5506/is_200309/ai_n21335475), Sep. 2003.*

*Primary Examiner* — Daniel Sullivan
*Assistant Examiner* — Barbara Frazier
(74) *Attorney, Agent, or Firm* — Sarah M. DeCristofaro; C. Brant Cook

(57) ABSTRACT

A paper tissue and products made from paper tissue, such as paper handkerchiefs, facial tissues, bath and cosmetic tissues, paper tissue wipes of any kinds and the like. The invention describes both the process for making a smooth and absorbent lotioned paper tissue, with high transferability of the lotion. The process steps comprises the steps of (a) providing a paper tissue web continuously moving next to a lotion application unit comprising at least one rotating surface, (b) transferring said lotion onto one rotating surface,'(c) expulsing said lotion from the said rotating surface into a stream of lotion droplets, by primarily the centrifugal force of the rotation of said rotating surface, (d) intercepting said paper tissue with said stream of lotion droplets. The invention also describes a paper tissue comprising a lotion distributed as discrete deposits on its surface. The deposits have a high local concentration of lotion and cover a relatively small area of the tissue.

12 Claims, 2 Drawing Sheets paper of the invention

(56) References Cited

U.S. PATENT DOCUMENTS

| | | | |
|---|---|---|---|
| 5,814,188 A * | 9/1998 | Vinson et al. | 162/109 |
| 5,869,075 A | 2/1999 | Krzysik | |
| 5,871,763 A | 2/1999 | Luu et al. | |
| 5,885,697 A | 3/1999 | Krzysik et al. | |
| 6,056,983 A * | 5/2000 | Broshi | 516/15 |
| 6,187,695 B1 | 2/2001 | Krzysik et al. | |
| 6,217,707 B1 | 4/2001 | Garvey et al. | |
| 6,231,719 B1 | 5/2001 | Garvey et al. | |
| 6,238,682 B1 | 5/2001 | Klofta et al. | |
| 6,261,580 B1 | 7/2001 | Lehrter et al. | |
| 6,432,268 B1 | 8/2002 | Burghardt | |
| 6,544,386 B1 * | 4/2003 | Krzysik et al. | 162/123 |
| 6,716,309 B2 | 4/2004 | Chuang et al. | |
| 6,752,905 B2 | 6/2004 | Hu et al. | |
| 6,756,520 B1 | 6/2004 | Krzysik et al. | |
| 6,758,943 B2 | 7/2004 | McConnell et al. | |
| 6,761,800 B2 | 7/2004 | Capizzi | |
| 6,805,965 B2 | 10/2004 | Liu | |
| 6,846,573 B2 | 1/2005 | Seydel | |
| 6,860,967 B2 | 3/2005 | Baumoller et al. | |
| 6,861,380 B2 | 3/2005 | Garnier et al. | |
| 6,887,350 B2 | 5/2005 | Garnier et al. | |
| 6,896,766 B2 | 5/2005 | Sarbo et al. | |
| 6,929,714 B2 | 8/2005 | Hu et al. | |

* cited by examiner

Figure 1a : paper of the invention
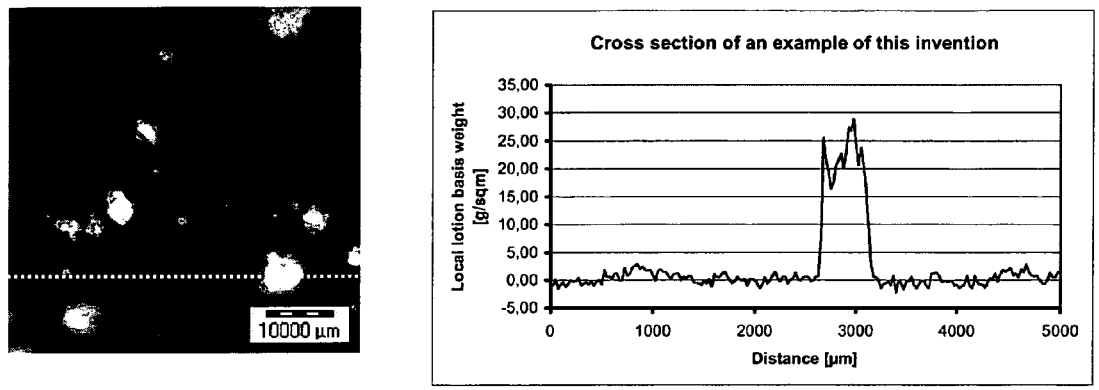
Fig 1b : Paper "Kleenex Balsam"
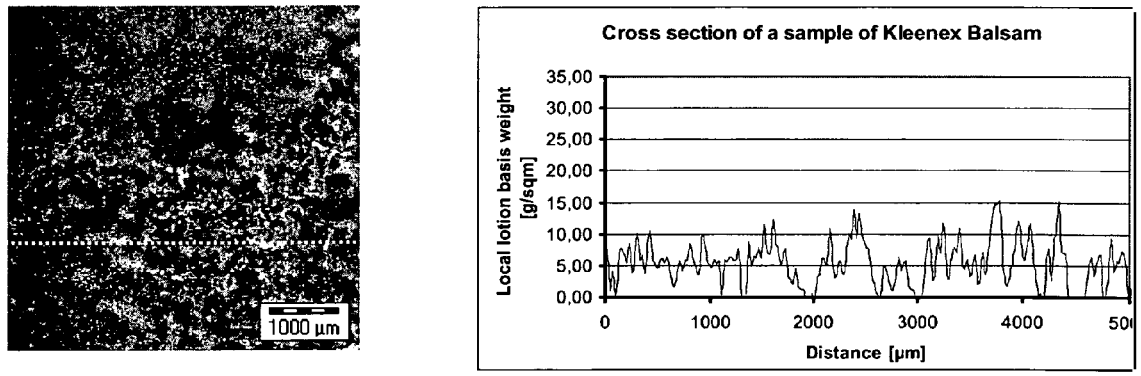

PAPER TISSUE WITH HIGH LOTION TRANSFERABILITY

CROSS REFERENCE TO RELATED APPLICATIONS

This application claims the benefit of U.S. Provisional Application Ser. No. 60/565,105 filed on Apr. 23, 2004.

FIELD OF THE INVENTION

The present invention relates to paper tissues, and products made from paper tissues, such as kitchen paper towels, toilet paper, facial tissues and disposable handkerchiefs, and methods for depositing lotion on the surface of the tissue. More particularly, the present invention relates to a tissue comprising a lotion having a particular distribution at its surface and methods for depositing the lotion on the tissue.

BACKGROUND OF THE INVENTION

Paper tissues sometimes called paper webs or sheets, tissues, tissue layers, paper plies or paper tissue webs, and products made there from, such as paper handkerchiefs, paper kitchen towel or bath tissue, toilet paper or facial tissues, find extensive use in modern society and are well known in the art. Paper tissues are generally made by the layering of cellulose fibers, in a wet form, onto a screen, with the addition of various additives or other ingredients, followed by a drying step. Other process steps, before, during or after the above-mentioned paper making steps are targeted at giving the desired properties to the tissue. Converting steps are aimed at creating a finished product from the paper tissue(s) and can include, for example embossing, lotion application, printing, combining, cutting, perforating, or folding.

Relatively thick and yet soft disposable paper products, namely in the form of paper handkerchiefs, are known. For example, Tempo™, sold by The Procter & Gamble Company, is a multi-ply paper product experienced as thick and soft and having a caliper of about 0.3 mm. A high calliper conveys the idea of high dry and wet strength to the consumer. A high wet strength, also referred to as wet burst strength, in particular prevents tearing or bursting which for a paper handkerchief in turn results in contamination of the user's hand with mucus or other body fluids.

A common way to enhance the smoothness of the tissue surface is to calender the material. Another way to improve the sensation of smoothness perceived by the users of paper tissue products, such as handkerchiefs, is to complement the composition of the paper tissue with some additives during the paper-making phase and/or during the converting phase. Alternatively or additionally, some additives have an effect on the skin of the user touching or using the paper tissue product, e.g. smoothening of the skin or hydration of the skin. Smoothening lotion (also called lotion, softening agent or softening composition in this document) is a generic term to describe those additives which (a) can have a softening effect on the tissue material, (b) preferably an effect on the skin, and (c) are partially transferred onto the skin of the user during use. It is usual industry practice to apply smoothening lotions on a native paper tissue surface at the converting stage of the manufacture of paper tissue products (as opposed to the paper-making stage of the manufacture). Usually, lotions are applied to the external surfaces of the paper tissue, but can also been applied to the internal surfaces. General knowledge on lotions and common application methods can be found in a number of publications. Among those the following are of particular relevance: U.S. Pat. No. 5,525,345, EP 0806157 and WO 02/066740. In WO 98/29605, Vinson et al. describe the application of a smoothening lotion onto a tissue in uniform discrete surface deposits in a configuration that enhances the tactile benefits delivered by the tissue. In WO 97/48854, Trokhan et al. describe a particular topography of the tissue (i.e. elevations) can be combined with a particular application of a lotion (for example on the said elevation) to enhance the softness of the tissue and creates tissue regions with differential properties.

Because smoothening lotions are usually of hydrophobic nature or contain hydrophobic compounds, the presence of the lotion at the surface of the paper tissue can have adverse effects on the properties of the paper tissue. First, the masking of the hydrophilic tissue surface by an hydrophobic lotion can reduce the absorbency of tissue or the speed of absorbency. Second, the lotion can migrate from tissue the surface through the paper tissue structure making the paper tissue less hydrophilic and making less lotion available at the surface to deliver the smoothening benefits to the skin. A traditional way to respond to that expected migration of the lotion over time is to use a relatively high amount of lotion to insure a certain availability of the lotion on the surface of the tissue, even after extended storage. However, this can create an excess of lotion on the freshly produced paper tissues triggering a negative greasy feeling during use (and reducing further more the absorbency of the paper tissue). Third, lotions that are coating the fibers are less likely to be released by the tissue during use and thus, less transferable to the skin of the user. This can be an economic disadvantage due to the relatively high cost of the lotion raw materials.

Accordingly, there is a need to provide a paper tissue exhibiting, preferably concurrently, a relatively high amount of lotion available at the surface of the tissue, and a relatively low amount of lotion in the inner structure of the tissue or tissue product, and a low overall hydrophobicity of the tissue, in order to maintain high absorbency, and a high transferability of the lotion onto the skin of the user, and a relatively low total amount of lotion in/on the tissue.

There is also a need for improved smoothening benefits of the tissue, improved absorbency of paper tissues, and improved transferability of the lotion to the users skin, without having one improvement being detrimental to the other.

SUMMARY OF THE INVENTION

In order to address the disadvantages of the prior art, the present invention provides a process of applying a lotion onto paper tissue comprising the steps of providing a paper tissue web continuously moving next to a lotion application unit including at least one rotating surface, transferring said lotion onto one rotating surface, expulsing said lotion from the said rotating surface into a stream of lotion droplets by primarily the centrifugal force of the rotation of said rotating surface, optionally reducing the angle of which the stream of droplet is expulsed, optionally by adjustable flaps adjusted to match the width of the desired application, intercepting said paper tissue with said stream of lotion droplets, and optionally collecting the lotion not intercepted by said paper tissue and recycling said collected lotion.

BRIEF DESCRIPTION OF THE DRAWINGS

FIG. 1 is a representation of the surface of a paper tissue comprising a lotion, as analyzed by the method described thereafter. FIG. 1a is a reference product "Kleenex Balsam", whereas FIG. 1b is a tissue product of this invention (lotion of example 1).

DETAILED DESCRIPTION OF THE INVENTION

Figure 2:
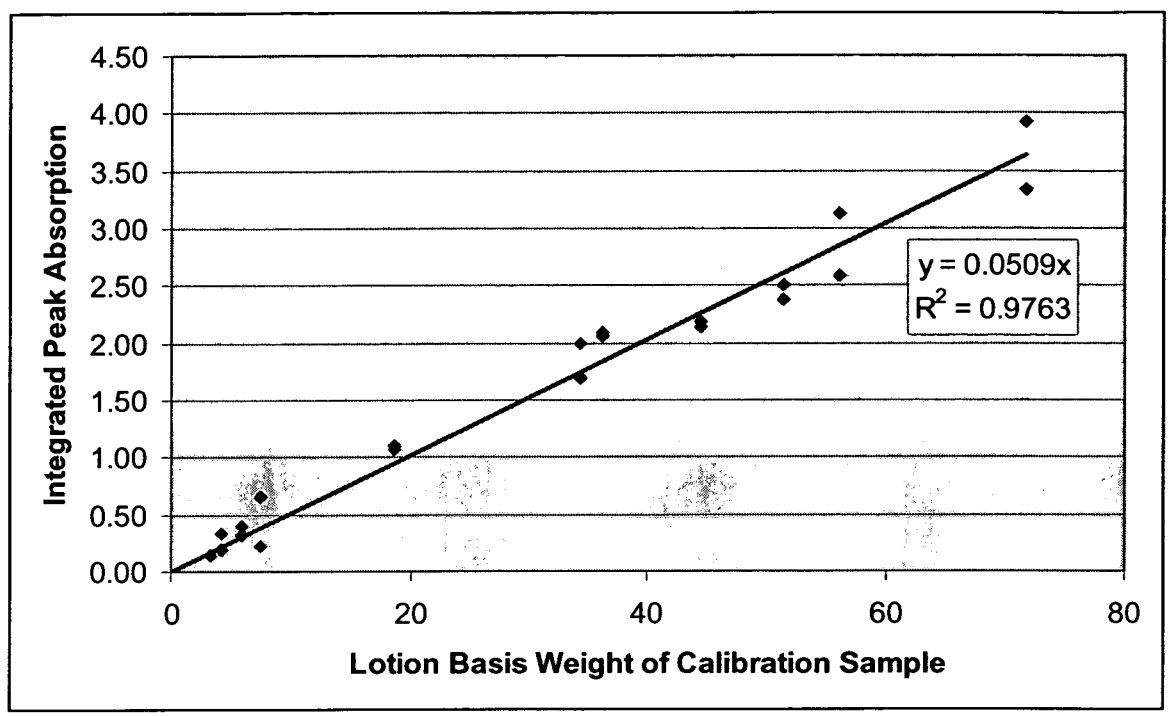
FIG. 2 is a calibration curve for the method described.

The present invention provides a paper tissue exhibiting a high level of surface smoothness and softness, high absorbency, a high strength and a high bulkiness. These apparently competing characteristics have been combined by following the concept of the present invention.

A "lotion" is a composition added to the tissue preferably at the converting phase in order to improved its softness/smoothness and preferably have smoothening effect on the skin. Some of the lotion can transfer from the tissue to the user's skin upon use of the paper tissue article. Lotion can be called alternatively smoothening or softening lotion or composition. The lotion may comprise softening/debonding agents, emollients, immobilizing agents and mixtures thereof. Suitable softening/debonding agents include quaternary ammonium compounds, polysiloxanes, and mixtures thereof. Suitable emollients include propylene glycol, glycerine, triethylene glycol, spermaceti or other waxes, petrolatum fatty acids, fatty alcohols and fatty alcohol ethers having from 12 to 28 carbon atoms in their fatty acid chain, mineral oil, namely silicone oil e.g. dimethicone and isopropyl palmitrat, and mixtures thereof. Suitable immobilizing agents include waxes, fatty alcohols, fatty acids, e.g. ceresin wax, microcrystalline wax, petroleum waxes, fisher tropsh waxes, paraffin waxes, stearyl alcohol and paraffins, polyhydroxy fatty acid esters, polyhydroxy fatty acid amides, and mixtures thereof. In most cases the lotions contain at least one immobilizing agent and an emollient. Lotions can be emulsions or dispersions. Other optional components include perfumes, antibacterial actives, antiviral actives, disinfectants, pharmaceutical actives, film formers, deodorants, opacifiers, astringents, solvents and the like. Particular examples of lotion components include camphor, thymol, menthol, chamomile extracts, aloe vera, calendula officinalis.

The terms "paper tissue", "paper tissue web", "tissue web", "tissue", "paper" and "web" are used interchangeably in this document. The present invention is useful with tissue paper in general, including but not limited to conventionally felt-pressed tissue paper; high bulk pattern densified tissue paper; and high bulk, uncompacted tissue paper and through-air dried paper. The tissue paper can be of a homogenous or multi-layered construction; and tissue paper products made therefrom can be of a single-ply or multi-ply construction. The tissue paper preferably has a basis weight of between about 10 g/m$^2$ and about 65 g/m$^2$, and density of about 0.6 g/cc or less. More preferably, the basis weight will be about 40 g/m$^2$ or less and the density will be about 0.3 g/cc or less. See Column 13, lines 61-67, of U.S. Pat. No. 5,059,282 (Ampulski et al), issued Oct. 22, 1991, which describes how the density of tissue paper is measured. (Unless otherwise specified, all amounts and weights relative to the paper are on a dry basis.) The papermaking fibers utilized for the present invention will normally include fibers derived from wood pulp. Other cellulosic fibrous pulp fibers, such as cotton linters, bagasse, etc., can be utilized and are intended to be within the scope of this invention. Non-cellulosic fibers such as those including starch and other polysaccharides. Synthetic fibers, such as rayon, polyethylene and polypropylene fibers, can also be utilized alone or in combination with natural cellulosic fibers. One exemplary polyethylene fiber that can be utilized is Pulpex®, available from Hercules, Inc. (Wilmington, Del.). Applicable wood pulps include chemical pulps, such as Kraft, sulfite, and sulfate pulps, as well as mechanical pulps including, for example, groundwood, thermomechanical pulp and chemically modified thermomechanical pulp. In addition to papermaking fibers, the papermaking furnish used to make tissue paper structures can have other components or materials added thereto as can be or later become known in the art. The types of additives desirable will be dependent upon the particular end use of the tissue sheet contemplated. For example, in products such as toilet paper, paper towels, facial tissues and other similar products, high wet strength is a desirable attribute. Thus, it is often desirable to add to the papermaking furnish chemical substances known in the art as "wet strength" resins.

The paper tissue of the present invention can be formed from a unique layer of material or can be a multi-layered tissue paper web. The terms "multi-layered tissue paper web, multi-layered paper web, multi-layered web, multi-layered paper sheet and multi-layered paper product" are all used interchangeably in the art to refer to sheets of paper prepared from two or more layers of aqueous paper making furnishes which are preferable comprised of different fiber types, the fibers typically being relatively long softwood and relatively short hardwood fibers as used in tissue paper making. The layers are preferable formed from the deposition of separate streams of dilute fiber slurries upon one or more endless foraminous surfaces. If the layers are initially formed on separate foraminous surfaces, the layers can subsequently combined when wet to form a multi-layered tissue paper web.

The "paper tissue product" of this invention are the finished products such a kitchen towels or paper handkerchiefs, made out of one or multiple plies of the above described paper tissues. Each ply of a multiply paper product can be made of diverse material or been manufactured in diverse ways at the paper making or converting steps. As used herein, the term "single-ply tissue product" means that it is comprised of one ply of tissue; the ply can be substantially homogeneous in nature or it can be a multi-layered tissue paper web. As used herein, the term "multi-ply tissue product" means that it is comprised of more than on ply of tissue. The plies of a multi-ply tissue product can be substantially homogeneous in nature of they can be multi-layered tissue paper webs.

"Lotion deposit" (or "deposit") is an area of relatively high lotion basis weight. A deposit is defined as an area of lotioned tissue with a local lotion basis weight of at least 10 g/sqm. Areas on the tissue with lower local basis weights are not part of a deposit. The local basis weight on the tissue is measured as described thereafter.

"Lotion basis weight of the deposits" is the concentration of lotion, expressed in grams per square meter, within the deposits of lotion on the tissue. This takes only into account the area of the deposits and the amount of lotion within the deposits. This is an average value of the deposits measured. The basis weight of a deposit is measured by the method described thereafter.

"Lotion basis weight of the tissue" is the overall concentration of lotion, expressed in grams per square meter, of lotion on the tissue (also referred as total or overall basis weight or concentration). The basis weight can be measured by any standard method, e.g. solvent extraction, or deducted from the process conditions (amount of lotion deposited on the tissue divided by the total area of the tissue).

"Size of deposits" is the average size of the deposits of lotion on the tissue, as measured by the method described thereafter.

"Area of tissue affected by lotion" is an area with a local lotion basis weight of more than 3 g/sqm as determined by the method described herein.

As described above, it is desirable to provide a smooth tissue that comprises a lotion able to be transferred easily into the skin of the tissue user. According to the present invention, the selection of the distribution of the lotion on the tissue, as a multitude of discrete deposits, can enhance the transferability of the lotion from the tissue onto the skin of the user. The higher that the local concentration (=basis weight) of the lotion within the deposits is, the higher the availability for transfer to the users skin upon use (=transferability). Indeed, with a relatively high local concentration of lotion in the discrete deposits, a relatively low amount of lotion is "bound" to the tissue fibers (fiber coating) and thus, relatively more lotion is "available" for transfer.

Deposits having a high concentration of lotion can be relatively easy to obtain with a relatively high total basis weight of lotion in the tissue. In some aspects however, the invention allows for both a lotion distribution on the tissue as discrete deposits, and a relatively high local concentration of the lotion in the deposits (=lotion basis weight of the deposits), and a relatively low total basis weight of lotion in the tissue. In some embodiments of the invention, the lotion basis weight in the deposits is at least 11 g/sqm, 13 g/sqm, 15 g/sqm, 17 g/sqm, 20 g/sqm, 25 g/sqm or more than 30 g/sqm. Also the total basis weight of lotion on the tissue is equal or less than 9 g/sqm, less than 6 g/sqm, less than 4.5 g/sqm, 3.0 g/sqm or less than 2 g/sqm.

In some embodiments, the ratio $R_3$ of lotion basis weight of the deposits to the total lotion basis weight of the tissue can be considered.

$$R_3 = \frac{\text{lotion basis weight of said deposits (in g/sqm)}}{\text{lotion basis weight of said tissue (in g/sqm)}}$$

In some embodiments, $R_3$ is at least 5, 7, 10, 15 or 20.

As previously mentioned, it has been found that it is also desirable to provide a tissue that has a relatively large area of "free absorbing space", i.e. area of tissue without lotion. Lotions are generally hydrophobic in nature and tend to reduce the absorbency of the tissue in the local area where the lotion is deposited. Alternatively, relatively hydrophilic lotions (e.g. emulsions) can provide for a local saturation of the tissue and thus a reduced residual absorption where the lotion is present. Accordingly, the smaller the cumulated area of the deposits is, the higher the absorbency of the tissue. In some aspects, the invention provides for relatively small deposits (that are also preferably relatively high in lotion concentration and relatively large areas that are not affected by the lotion.

Deposits of small size can be relatively easy to obtain with low total basis weight of lotion on the tissue. The present invention however provides for both relatively small deposits and relatively high total basis weight of lotion on the tissue.

In some embodiments the size (area) of the deposits, as determined by the method described in this document, A ratio R can be considered. R is defined as:

$$R_1 = \frac{\text{Area of said portions affected by said lotion (in sqcm)}}{\text{Total area of said tissue (in sqcm)} \times \text{said lotion basis weight of said tissue (in g/sqm)}}$$

As per some embodiments of the present invention, R is less than 0.15 sqm/g, less than 0.13 sqm/g, less than 0.10 sqm/g, less than 0.08 sqm/g or less than 0.05 sqm/g.

In certain embodiments, the total basis weight of lotion on the tissue is at least 0.3 g/sqm, 0.6 g/sqm, 1.0 g/sqm, 1.5 g/sqm or 2.5 g/sqm. In some embodiments, the absolute amounts of lotion in the deposits and in the tissue can be considered. A ratio $R_2$ is defined in that respect:

$$R_2 = \frac{\text{lotion basis weight of said deposits (in g/sqm)} * \text{area of said deposits (sqm)}}{\text{lotion basis weight of said tissue (in g/sqm)} * \text{total area of said tissue (sqm)}}$$

In these embodiments, $R_2$ is at least 0.02, 0.05, 0.1, 0.2, 0.4 or more than 0.8.

In some embodiments, the invention relates to the proportion of "open area" (=areas not effected/covered by the lotion) in the tissue. A ratio $R_4$ is defined as $$R_4 = \frac{\text{Area of said portions affected by said lotion (in sqcm)}}{\text{Total area of said tissue (in sqcm)}}$$

It has been found that such ratio $R_4$ can be less than 0.4, less than 0.3, less than 0.2, less than 0.15 or less than 0.1

In some embodiments the invention relates to the percentage P1 of the total area covered with deposits, that is covered with deposits of a size of at least 0.005 sqmm, 0.01 sqmm, larger than 0.025 sqmm or between 0.03 sqmm and 3 sqmm. It has been found that this percentage P1 is preferably larger than 20%, larger than 50%, larger than 70% and larger than 85%.

In some embodiments, the invention is related to a multiply tissue product. When the multiply tissue product comprises 2 plies, it has been found to be desirable that at least one of the external surfaces (outwardly orientated surfaces) has more lotion than its corresponding internal surface (inwardly orientated surfaces). This can be determined by scanning electron microscopy. When the multiply tissue product has at least 3 plies, it has been found that the lotion transferability is suitable when at least 60%, at least 70%, at least 80% or at least 90% of the lotion is located one of the outer plies. Indeed, the lotion present on the inner ply(ies) contributes much less in the transfer of the lotion to the users skins.

Lotion:

The present invention as described here particularly focuses on smoothening lotion. It should be noted that any type of additives or compound could be applied by the described process, as long as the physical characteristics (e.g. melting point, viscosity), and the application temperature are adjusted to obtain the desired distribution pattern of the applied additives or compounds at the surface of the paper tissue. These additives or compounds could include: hydration lotion, soap, moisturizers, sun-protection, make-up removal ingredients, anti-aging, disinfectants, or more generally additives/compounds in the cosmetic and therapeutic fields, detergents, soaps, waxes, cleaning additives and more generally compounds for the cleaning, maintenance, protection and treatment of objects, surfaces or mechanical parts.

Lotions are in most instances of heterogeneous composition. They may contain solids, crystalline gel structures, polymeric material below glass point, a multiplicity of phases (such as oily and water phase) and/or emulsified components. It may be difficult to determine precisely the melting temperature of the lotion, i.e. difficult to determine the temperature of transition between the liquid form, the quasi-liquid from, the quasi-solid form and the solid form. The terms melting temperature, melting point, transition point and transition temperature are used interchangeably in this document and have the same meaning.

For the purpose of this invention it is considered that not only the melting temperature relates to the definition of the form or state of the lotion (liquid, solid, quasi-liquid, quasi-solid), but also its rheological properties. For the purpose of this invention, it is defined that liquid or quasi-liquid lotion are able to flow, move, and migrate, for example under the force encountered during the process of application. Solid or quasi-solid lotions are not able to flow freely and are somewhat immobilized at their location. For example a lotion will be said liquid or quasi-liquid if it can be fed onto the rotating surfaces and expulsed there from under the used process conditions. A lotion will be said solid or semi-solid if it does not significantly freely migrates from the surface into the inner structure of the tissue at room temperature, i.e. 23° C. until the product is usually used.

The lotion may comprise a surface treating agent. Nonlimiting examples of suitable surface treating agents that may be included in the lotion can be selected from the group consisting of: polymers such as polyethylene and derivatives thereof, hydrocarbons, waxes, oils, silicones (polysiloxanes), quaternary ammonium compounds, fluorocarbons, substituted $C_{10}$-$C_{22}$ alkanes, substituted $C_{10}$-$C_{22}$ alkenes, in particular derivatives of fatty alcohols and fatty acids (such as fatty acid amides, fatty acid condensates and fatty alcohol condensates), polyols, derivatives of polyols (such as esters and ethers), sugar derivatives (such as ethers and esters), polyglycols (such as polyethyleneglycol) and mixtures thereof.

The lotion may comprise oils and/or emollients and/or waxes (any and all of which may be a transferable agent) and/or immobilizing agents. In one example, the lotion comprises from about 10% to about 90% of an oil and/or liquid emollient and from about 10% to about 50% of immobilizing agent and/or from about 0% to about 60% of petrolatum and optionally the balance of a vehicle.

The lotion may be heterogeneous. They may contain solids, gel structures, polymeric material, a multiplicity of phases (such as oily and water phase) and/or emulsified components. It may be difficult to determine precisely the melting temperature of the lotion, i.e. difficult to determine the temperature of transition between the liquid form, the quasi-liquid from, the quasi-solid form and the solid form. The terms melting temperature, melting point, transition point and transition temperature are used interchangeably in this document and have the same meaning.

The lotion may be semi-solid, of high viscosity so they do not substantially flow without activation during the life of the product or gel structures.

The lotion may be shear thinning and/or they may strongly change their viscosity around skin temperature to allow for transfer and easy spreading on a user's skin.

The lotion may be in the form of emulsions and/or dispersions.

In one example of a lotion, the lotion has a water content of less than about 20% and/or less than about 10% and/or less than about 5% or less than about 0.5%.

In another example, the lotion may have a solids content of at least about 15% and/or at least about 25% and/or at least about 30% and/or at least about 40% to about 100% and/or to about 95% and/or to about 90% and/or to about 80%.

Nonlimiting examples of suitable oils and/or emollients include glycols (such as propylene glycol and/or glycerine), polyglycols (such as triethylene glycol), petrolatum, fatty acids, fatty alcohols, fatty alcohol ethoxylates, fatty alcohol esters and fatty alcohol ethers, fatty acid ethoxylates, fatty acid amides and fatty acid esters, hydrocarbon oils (such as mineral oil), squalane, fluorinated emollients, silicone oil (such as dimethicone) and mixtures thereof.

Immobilizing agents include agents that are may prevent migration of the emollient into the paper tissue such that the emollient remain primarily on the surface of the paper tissue and/or sanitary tissue product and/or on the surface treating composition on a surface of the paper tissue and/or sanitary tissue product and facilitate transfer of the lotion to a user's skin. Immobilizing agents may function as viscosity increasing agents and/or gelling agents.

Nonlimiting examples of suitable immobilizing agents include waxes (such as ceresin wax, ozokerite, microcrystalline wax, petroleum waxes, fisher tropsh waxes, silicone waxes, paraffin waxes), fatty alcohols (such as cetyl and/or stearyl alcohol), fatty acids and their salts (such as metal salts of stearic acid), mono and polyhydroxy fatty acid esters, mono and polyhydroxy fatty acid amides, silica and silica derivatives, gelling agents, thickeners and mixtures thereof.

In one example, the lotion comprises at least one immobilizing agent and at least one emollient.

In one example, the lotion comprises a sucrose ester of a fatty acid.

The lotion may be comprise a transferable agent and thus be considered a transferable lotion. A transferable lotion comprises at least one transferable agent that is capable of being transferred to an opposing surface such as a user's skin upon use. In one example, at least 0.1% of the transferable lotion present on the user contacting surface transfers to the user's skin during use. The amount of transferable composition that transfers to a user's skin during use can be determined by known methods such as by tape stripping the skin 3 times, after use of the paper tissue and/or sanitary tissue product by the user, with Tegaderm Tapes, available from 3M, and analyzing the tapes for the transferable composition or a component within the transferable composition assuming all components of the transferable composition transfer equally.

Other optional components that may be included in the lotion include vehicles, perfumes, especially long lasting and/or enduring perfumes, antibacterial actives, antiviral actives, disinfectants, pharmaceutical actives, film formers, deodorants, opacifiers, astringents, solvents, cooling sensate agents, and the like. Particular examples of lotion components include camphor, thymol, menthol, chamomile extracts, aloe vera, calendula officinalis, alpha bisalbolol, Vitamin E, Vitamin E acetate.

In one example, the lotion is present on the surface of the paper tissue and/or sanitary tissue product and/or on the surface treating composition present on the surface of the paper tissue and/or sanitary tissue product at a level of at least about 0.5 $g/m^2$ and/or at least about 1.0 $g/m^2$ and/or at least about 1.5 $g/m^2$ per user contacting surface. In another example, the lotion is present on the surface of the paper tissue and/or sanitary tissue product and/or on the surface treating composition present on the surface of the paper tissue and/or sanitary tissue product at a level of from about 0.5 g/m² and/or from about 1.0 g/m² and/or from about 1.5 g/m² to about 10 g/m² and/or to about 8 g/m² and/or to about 6 g/m² per user contacting surface.

As used herein a "vehicle" is a material that can be used to dilute and/or emulsify agents forming the surface treating composition and/or lotion to form a dispersion/emulsion. A vehicle may be present in the surface treating composition and/or lotion, especially during application of the surface treating composition and/or to the paper tissue. A vehicle may dissolve a component (true solution or micellar solution) or a component may be dispersed throughout the vehicle (dispersion or emulsion). The vehicle of a suspension or emulsion is typically the continuous phase thereof. That is, other components of the dispersion or emulsion are dispersed on a molecular level or as discrete particles throughout the vehicle.

Suitable materials for use as the vehicle of the present invention include hydroxyl functional liquids, including but not limited to water. In one example, the lotion comprises less than about 20% and/or less than about 10% and/or less than about 5% and/or less than about 0.5% w/w of a vehicle, such as water. In one example, the surface treating composition comprises greater than about 50% and/or greater than about 70% and/or greater than about 85% and/or greater than about 95% and/or greater than about 98% w/w of a vehicle, such as water.

It has been found that a suitable lotion of the present invention has a water content of less than 20%, less than 10%, less than 5% or less than 0.5%.

Example 1 of Lotion Formulation

It has been found that the present invention is of particular efficacy when the lotion has the following composition (in weight/weight percent):

| | |
|---|---|
| Stearyl Alcohol CO1897* | 40% |
| Petrolatum Snowwhite V28EP** | 30% |
| Mineral oil Carnation** | 30% |

*Available from Procter&Gamble Chemicals, Cincinnati, USA
**Available from Crompton Corporation The formulation has a melting point of about 51° C. and a melt viscosity at 56° C. of about 17 m*Pas measured at a shear rate of 0.1 1/s. The mineral oil used in this formulation has a viscosity of about 21 mPa*s at 20° C. The formulation was applied in equal amounts to both outer surfaces of the tissue substrate described in the tissue paper example 1 at total add-on levels of 3.6 g/sqm, 4.2 g/sqm, 6 g/sqm, 7.2 g/sqm, 8.4 g/sqm and 11.4 g/sqm. In a consumer use test all products provided a noticeable lotion feel and were preferred by consumers for skin caring properties and for not being rough vs. the untreated base tissue product. It is hypothesized that the lotion is particularly suited to provide the lotion deposits and distribution as claimed in the present invention due to the high level of fatty alcohol in the formulation that helps to stabilize the desired structure. It is believed that the present invention works best if more than 30%, more than 35% or more than 40% of fatty alcohol are present in the formulation if low viscosity oils are employed.

Example 2 of Lotion

The following composition (in weight percent) has also been found of particular efficacy, as part of invention but also independently.

| | Composition | Viscosity at 75° F. |
|---|---|---|
| SEFOSE 1618S* | 80% | 418 mPas |
| Stearyl alcohol CO1897** | 20% | solid |

*Sucrose esters of fatty acids, available from Procter&Gamble Chemicals, Cincinnati, USA
**Available from Procter&Gamble Chemicals, Cincinnati, USA It is hypothesized that the lotion is particularly suited to provide the lotion deposits and distribution as claimed in the present invention. Independently, it is speculated that the relatively high viscosity of the oil used in the lotion provides specific benefits in regard to the efficacy of the lotion. The above formulation is a shear sensitive semi-solid at room temperature with a melting point of about 50° C. and a melt viscosity of about 50 mPas at 56° C. at a shear rate of 0.1/s. The oil used in this formulation (SEFOSE 1618S) has a fluid viscosity of about 418 mPa*s at 24° C.

The above formulation was applied equally to both outer surfaces of the substrate described in tissue paper example 1 with the equipment and process described further below. Total add-on level was 6 g/sqm, 3 g/sqm on each surface.

The product was then submitted to a consumer use test together with the same tissue product but made with the formulation described in Example 1 instead of the formulation described in this example. On average, the panelists rated the products made with the formulation of this example preferred and more pleasant for skin feel than the formulation of example 1. In particular the lotion feel is rated less waxy than the lotion of example 1. It is speculated that the high viscosity of the oil causes a more pleasant skin feel. It is believed that oils or oil mixtures with viscosities at 20° C. and a shear rate of 0.1 mPa*s above 30 mPas, preferably above 40 mPas, more preferably above 60 mPa*s, even more preferably above 100 mPas, 150 mPa*s, 200 mPa*s, 250 mPa*s, 300 mPa*s and most preferably above 350 mPa*s will generate a feel benefit compared to lower viscosity oils or oil mixtures in the formulation. For shear thinning oils or oil mixtures preferred viscosities can be even higher. Suitable classes of oils include but are not limited to mineral oil, hydrocarbon based oils, vegetable oils, esters, ethers, alcohols, ketones, silicone oils, glycols and polyglycols or mixtures thereof and mixtures with low viscosity base oils.

It is further speculated that the high melt viscosity of the formulation helps to increase the lotion transfer of the final product by minimizing the formulation to dissipate into the tissue even when formulated with low amounts of an immobilizing agent. In this example 20% of stearyl alcohol are sufficient to immobilize the formulation sufficiently fast after application. It is believed it is this low amount of immobilizing agent that reduces the waxy feel of the formulation. It is further believed that a melt viscosity at the application temperature of higher than 20 mPas, preferably 40 mPas, even more preferably 60 mPa*s, 80 mPa*s, 100 mPa*s, 150 mPa*s, 200 mPa*s, 250 mPa*s, 300 mPa*s, preferably less than 2000 mPa*s, will improve lotion transfer of the final product. It is believed that this is due to a relatively slowed down penetration of the lotion into the web during the solidification process right after application of the melt. It is further hypothesized that a strong temperature and/or shear dependence of the viscosity of the oil used, or the mixture of oils used, will help to improve lotion transfer of the final product.

Contrary, it has been found that the following formulation dissipates much more into the tissue when applied to the web with the same process and quantity as the first formulation of this example. It is speculated that this is caused by the absence of a high viscosity oil:

| | | |
|---|---|---|
| Stearyl Alcohol CO1897* | 20% | |
| Petrolatum Snowwhite V28EP** | 40% | |
| Mineral oil Carnation** | 40% | |

*Available from Procter&Gamble Chemicals, Cincinnati, USA
**Available from Crompton Corporation Example 3 of Lotion The following composition (by weight percent) has also been found of particular efficacy, as part of invention but also independently. It is hypothesized that the lotion is particularly suited to provide the lotion deposits and distribution as claimed in the present invention. Independently, it is speculated that the relatively high viscosity of the oil used in the lotion provides specific benefits in regard to the efficacy of the lotion.

| | Composition | Viscosity at 75° F. |
|---|---|---|
| SEFOSE 1618S* | 75% | 418 mPas |
| Stearyl alcohol CO1897** | 25% | Solid |

*Sucrose esters of fatty acids, available from Procter&Gamble Chemicals, Cincinnati, USA
**Available from Procter&Gamble Chemicals, Cincinnati, USA The above formulation is a shear sensitive semi-solid at room temperature with a melting point of about 50° C. and a melt viscosity of about 50 mPas at 56° C. and a shear rate of 0.1/s. The oil used in this formulation (SEFOSE 1618S) has a fluid viscosity of about 418 mPa*s at 24° C.

The above formulation was equally applied to both outer surfaces of the tissue substrate described in tissue paper example 1 with the equipment and process described further. Total add-on level was 4.2 g/sqm, 2.1 g/qm on each outer surface. The product was then submitted to a consumer use test together with the same tissue product but made with the formulation described in Example 1 instead of the formulation described in this example. On average, the panelists rated the products made with the formulation of this example worse for skin feel related attributes than the formulation of example 2. In particular the formulation was perceived as waxier. However, even though less lotion was applied than in example 2, the products of this examples were rated similar for the amount of lotion on the tissue. It is speculated that the higher amount of fatty alcohol causes a waxier feel and the lotion to be more feelable.

Example 4 of Lotion

The following composition has also been found of particular efficacy, as part of invention but also independently. It is hypothesized that the lotion is particularly suited to provide the lotion deposits and distribution as claimed in the present invention. Independently, it is speculated that the particular ingredients used provide significant benefits as for the perception of the lotion by the users.

| | |
|---|---|
| Stearyl Alcohol CO1897* | 39.9% |
| Petrolatum Snowwhite V28EP** | 29.9% |
| Mineral oil Carnation** | 29.9% |
| 2-Isopropyl-N,2,3-trimethylbutyramide (WS23)*** | 0.3% |

*Available from Procter&Gamble Chemicals, Cincinnati, USA
**Available from Crompton Corporation
***Available from Millennium Specialty Chemicals The above formulation was applied equally to both outer surfaces of the tissue substrate described under tissue substrate example 1. Total add-on level was 6 g/sqm, 3 g on each outer surface. The product only had a very faint minty scent. The product was then submitted to a consumer use test together with the tissue product of Example 1 with the same add-on level. A significantly higher proportion of panelists claimed to perceive a refreshed feeling and to be able to breathe more freely when using the product of this example compared to the product of example 1. It is speculated that the presence of WS-23 is causing the above mentioned benefits. It is further speculated that similar benefits can be obtained with other relatively odorless compounds ("cooling sensates") when applied to the tissue. Suitable classes of compounds include, but are not limited to, acyclic or cyclic carboxamides, preferably derivatives of 2-Isopropyl-2,3-dimethylbutyric acid, more preferably derivatives of 2-Isopropyl-2,3-dimethylbutyramide, and most preferably 2-Isopropyl-N,2,3-trimethylbutyramide, menthane derivatives, preferably 3-substituted p-menthane derivatives, more preferably p-Menthane-3-carboxamide and its derivatives, menthol derivatives like esters, ethers or amides, or Menthone derivatives. It is further speculated that the perceived effect will be stronger if the "cooling sensate" is a volatile compound and can evaporate from the formulation. A suitable method for the evaluation of the volatility of an potential "cooling sensate" is gas chromatographic head-space analysis.

Example 5 of Lotion

The following composition has also been found of particular efficacy, as part of invention but also independently. It is hypothesized that the lotion is particularly suited to provide the lotion deposits and distribution as claimed in the present invention. Independently, it is speculated that the particular ingredients used provide significant benefits as for the perception of the lotion by the users.

| | |
|---|---|
| Stearyl Alcohol CO1897* | 39.9% |
| Petrolatum Snowwhite V28EP** | 29.9% |
| Mineral oil Carnation** | 29.9% |
| 2-Isopropyl-N,2,3-trimethylbutyramide (WS23)*** | 0.3% |
| Perfume Refresh 1813BC**** | 0.02% |

*Available from Procter&Gamble Chemicals, Cincinnati, USA
**Available from Crompton Corporation
***Available from Millennium Specialty Chemicals
****Available from IFF International Flavors & Fragrances The above formulation was applied equally to both outer surfaces to the tissue substrate described under tissue paper example 1 a level of 3 g/sqm on both outer sides of the substrate. Total add-on level was 6 g/sqm. The product only had a refreshing scent.

The product was then submitted to a consumer use test together with the tissue product of Example 3 with the same add-on level. On average panelists perceived a higher level of refreshed feeling with the products of this example, compared to the product of example 4. The product was also submitted to scent panel together with the same product lacking 2-Isopropyl-N,2,3-trimethylbutyramide.

It is speculated that the presence of WS-23 is causing the above mentioned benefits, in particular that it enhances and complements the perfume perception in a synergistic manner. It is further speculated that similar benefits can be obtained with other relatively odorless "cooling sensates", when applied to the tissue in combination with a perfume to the tissue. Suitable classes of compounds include, but are not limited to, acyclic or cyclic carboxamides, preferably derivatives of 2-Isopropyl-2,3-dimethylbutyric acid, more preferably derivatives of 2-Isopropyl-2,3-dimethylbutyramide, and most preferably 2-Isopropyl-N,2,3-trimethylbutyramide, menthane derivatives, preferably 3-substituted p-menthane derivatives, more preferably p-Menthane-3-carboxamide and its derivatives, menthol derivatives like esters, ethers or amides, or Menthone derivatives. It is further speculated that the effect will be stronger if the "cooling sensate" is a volatile compound and can evaporate from the formulation. A suitable method for the evaluation of the volatility of an potential "cooling sensate" is gas chromatographic head-space analysis.

Application Process:

The process steps of the present invention relate to the above mentioned "converting steps" of the manufacturing of paper tissue products. The application of the lotion can be done via the use of rotating surfaces from which the lotion is expulsed to impact the paper tissue. The temperature of the rotating surface is selected to match the composition of the lotion, in order to at least insure the combination of two phenomena: First, the expulsion disperses the lotion into a stream (or cloud) of droplets. The stream of droplets, when impacting the tissue, induces a particular distribution of the lotion onto the tissue. The lotion is distributed as a high number of relatively small discrete deposits. The overall distribution of the deposits onto the affected is substantially macroscopically uniform in the area covered. Second, the droplets are expulsed in a liquid or quasi-liquid form and are in a solid or quasi-solid form when on the impacted tissue. The liquid form or quasi-liquid form is desirable to insure smooth processing conditions (flow of the lotion through the pipes of the equipment and continuous flow onto the rotating surfaces). The solid or quasi-solid form of the lotion, after the interception by the tissue, presents the benefit to reduce the penetration of the droplets into the structure of the tissue. The droplets have a tendency to stay immobilized at the surface of the tissue, without penetrating deeply into the network of paper fibers. This induces a high transferability of the lotion.

The reduced penetration of the lotion within the inner structure of the tissue can be measured by a detection of the lotion present on the opposite sides of the tissue. In some embodiments of the present invention, the lotion is less detectable on the surface of the tissue opposite to the surface directly impacted by the lotion.

In one embodiment of the invention, the lotion is applied by a unit presenting a series of rotating surfaced. Examples of units able to deliver substantially the intended process, can be found in WO-0234519 and WO-234520, both applied by Weitmann and Konrad GmBh from Germany.

The lotion is pumped onto rotating surfaces which upper surfaces are generally orientated perpendicularly to the surface of the running paper tissue (although some advantages can prophetically be found in having an angle different from 90 degrees between the surface of the rotating surfaces and the running tissue). Flaps and covers are built optionally into the unit to open only the desirable angle of projection for each rotating surface onto the tissue. A collection system may collect the lotion intercepted by the flaps and covers and may feed it back onto the rotating surfaces (with the advantages of reducing the quantity of wasted lotion). The whole unit or certain parts of it (such as the rotating surfaces and/or the feeding pipes) are maintained at a determined temperature in a controlled way. The centrifugal force created by the rotation of the rotating surfaces onto the thereon fed lotion (possibly complemented by the force created by the flow of the lotion from the feeding lines), expulses the lotion and disperse it into a cloud of fine droplets. In one embodiment of the invention, it is foreseen that an electrostatic means can helping the expulsion and/or guiding the droplet onto the paper tissue (such electrostatic mean can create an electrostatic field between the rotating surface and the tissue paper and/or between other parts of the equipments). Optionally flaps and covers cut off the projection to limit the width of the application. The flaps and/or covers can be adjustable to the desired process conditions. Optionally, over pressure or under pressure in the application unit, relative to the outside environment are used to facilitate the application of the lotion.

The speed of the rotating surface can be controlled and adjusted easily to the desired process conditions. More preferably the speed control and adjustment can be performed on subgroups of rotating surfaces (most preferably on individual rotating surfaces).

The application unit may comprise a system to easily control and adjust the temperature of application to the desired value. The temperature of the unit may be set between 0 and 20 degrees Celsius above and below the melting temperature of the lotion between 0 and 10, between 0 and 5 and between 0 and 3 above and below the melting temperature of the lotion. Other ranges can include 0.5 to 2 and 1 to 2 degrees Celsius above and below the melting temperature of the lotion.

The flow of the lotion fed onto the rotating surfaces can be controlled and adjusted easily to the desired process conditions. More preferably the control and the adjustment of the flow can be done on independent subgroups of rotating surfaces (most preferably on each individual rotating surface.

The rotating surfaces of the above described present a generally flat surface as to enable an unobstructed flow of the lotion from the feeding point to the outer edge of the rotation surface. However, uneven, patterned, or structured surfaces (for example with parallel or spiraling grooves) can also be used. Further, multiple feeding points or areas can also be used, as described.

Optional flaps and covers can restrict the direction of projection/expulsion of the lotion to the desired direction, i.e. toward the tissue, by reducing the open angle through which the lotion is expulsed. One or multiple openings per rotating surface are possible.

Multiple Rotating Surfaces:

The number of rotating surfaces is at least one but is adapted to cover the complete desired width of lotion application or to adapt the amount of lotion delivered to the tissue for the desired purpose. Various rotating surfaces can be positioned substantially in a raw, thus covering part or the entire width of the paper tissue. Alternatively or additionally, superimposed rotating surfaces can be contemplated, creating for example 2 (or 3 or 4 or more) superimposed rows of rotating surfaces. In general terms, the position of the rotating surfaces can be freely selected, preferably in subgroups or more preferably individually, for the intended purpose. Preferably the number of rotating surface per meter is between 2 to 40, between 3 and 20, or between 5 and 10. The number of rows of rotating surface is preferably between 1 and 5, between 1 and 2, or 1.

Overlaps of Application:

The application of the lotion can create zones where the projections coming from more than one rotating surface overlap. This overlapping effect can be reduced or eliminated by adjusting the configuration of the rotating surfaces and/or the optional flaps and covers. Alternatively, one can contemplate to induce overlapping projection of lotion in order to increase the amount of lotion on all (or part) of the width of the tissue, versus the amount deposited without overlapping. In one embodiment of the invention, one or a multiplicity of zones (in the width of the tissue) are created with overlapping projections. This is done by carefully selecting the overlap of the projection, via the adjustment of the position of the rotating surface(s) and/or of the optional flaps or covers. The zone(s) of the tissue thereby created have an increased amount of lotion (compared to the application without overlap). One can select the location of the zone(s) to functionally achieve optimized end benefits (such as reduced total use of lotion while keeping a high amount of lotion transfer in use, high transfer in the center tissue zone, or—in a general manner—optimized protection of the body part in contact with the tissue during use).

Alternatively, overlapping can be created to equalize the amount of lotion applied (i.e. to have a homogeneous basis weight of lotion applied throughout the width of the tissue). This can be particularly relevant when each individual rotating surface provides an uneven (or non-homogeneous) distribution. The basis weight is defined as the weight-amount of lotion applied to the tissue per unit of area of tissue. A homogeneous distribution is defined by the fact that substantially the same basis weight of lotion can be found each area of the tissue, independently from the position of the area considered in the width of the tissue. Preferably, the streams of droplets coming from the various rotating surfaces are set to create overlaps adjusted in a way that induces a substantially homogeneous distribution of droplets in the width of the tissue. Preferably the substantially homogeneous distribution creates a range of basis weights measured in the width of the tissue, of not more than +/−40% of the average basis weight, +/−20%, +/−10%, +/−5%, or +/−2%.

Alternatively, in another embodiment of the present invention, the application of the lotion is purposely adjusted to create a non-homogeneous distribution of lotion in the width of the tissue. The rotating surfaces creating overlapping projections of droplets in the width of the web can be positioned in a manner that the streams of droplets do not interfere, e.g. in different heights. Alternatively the total width of the application is adjusted to cover almost exactly the width of the paper tissue.

Gaps:

The rotating surface and/or the optional flaps and/or the covers can be positioned in such a way that creates at least one zone on the tissues that is not effected by the lotion. The end result is a paper tissue that has zone(s) with lotion and zone(s) without lotion. Preferably the rotating surface(s) and/or the optional flaps and/or the covers are adjusted to not leave any gaps in the width of the application onto each individual zone of material later creating to one unique finished product (such as, for example, one paper handkerchief). Most preferably, the equipment is set to leave a defined gap between the zones of material intended to later create one unique finished product (such as, for example, one paper handkerchief). Of note, it is common industry practice to cut more than one finished product in the width of the converted tissue (this is however not essential for the present invention). Therefore, in certain embodiments, the outer edges of the finished products (for example, the edges of the paper handkerchiefs), are free of lotion whereas the center zone of the finished product comprises a continuous zone with lotion.

Distribution of the Droplets of Lotion Onto the Surface of the Paper Tissue:

As indicated above the results of the method of application is a cloud (or a stream) of fine droplets of lotion effecting the surface of the paper tissue. With the movement of the paper tissue (or paper tissue web) relative to the window of application of the lotion, the droplets creates a discrete deposits of lotion at the surface of the paper tissue. Of note, for the purpose of the present invention and in this document, the term "droplet" refers to the individual units of lotion being expulsed form the rotation surface The term "deposits" (equally referred to as "flakes") refers to the unit of lotion resulting from the impact of the droplets onto the tissue. One can easily understand that the shape and size of the droplets are not identical to those of the deposits (or flakes). The method for measuring the size of the droplets and of the deposits are expressed toward the end of this documents, under the paragraph "methods".

Preferably a relatively large proportion of the droplets created by the process of the present invention is larger than $3*10^{-4}$ μl, larger than $3*10^{-3}$ μl, larger than $10^{-2}$ μl, between 3 μl and $3*10^{-4}$ μl, or between 0.3 μl and 0.03 μl.

Droplet volume can be calculated from the droplet diameter which can be measured by particle size analysis as described below. A relatively large proportion of droplets means at least more than 20%, preferably more than 50% even more preferably more than 70% and most preferably more than 90% of the droplets by weight.

EXAMPLES

Paper Tissue Example 1

The tissue paper used in the following examples is a conventional wet pressed, homogeneous, dry creped tissue paper with a basis weight of about 15.4 g/sqm. The paper web has a composition of about 40% Northern Softwood Kraft and 60% Eucalyptus. Following the papermaking, four sheets of paper are combined together in an offline combining operation. The pre-combined 4-ply parent roll is subsequently converted into a 4-ply tissue product. The 4-ply parent roll is unwound and subjected to calandering between two smooth steel calender rolls followed by high pressure embossing to achieve ply bonding. The majority of the tissue paper remains unaffected by the high pressure embossing. Finally the tissue was cut in machine direction, followed by cutting in cross direction into sheets of approximately 21 cm×21 cm, folded, stacked into stacks of 9 sheets and packed into individual pocket packs. The 4-ply paper tissue product obtained by the above described process had a basis weight of approximately 60 g/sqm (not including any lotion applied), a thickness of 0.27 mm, a machine direction strength of 1280 g/in, a cross direction strength of 610 g/in, and a wet burst of about 200 g. It contained a wet strength agent and a dry strength agent.

Paper Tissue Example 2

The tissue paper used in the following examples is a conventional wet pressed, layered, dry creped tissue paper with a basis weight of about 14.6 g/sqm. The outer layer contains about 100% Eucalyptus fiber whereas the inner layer is composed of a furnish mix of about 85% Northern Softwood Kraft, 10% CTMP and about 5% Eucalyptus fiber. Both layers are of about equal basis weight (symmetrical layer split). Following the papermaking, four sheets of paper are combined together in an off line combining operation. The pre-combined 4-ply parent roll is subsequently converted into a 4-ply tissue product. The 4-ply parent roll is unwound and subjected to calendering between two smooth steel calender rolls followed by high pressure embossing to achieve ply bonding. The majority of the tissue paper remains unaffected by the high pressure embossing. Finally the tissue was cut in machine direction, followed by cutting in cross direction into sheets of approximately 21 cm×21 cm, folded, stacked into stacks of 9 sheets and packed into individual pocket packs. The 4-ply paper tissue product obtained by the above described process has a basis weight of approximately 60 g/sqm (not including any lotion applied), a thickness of 0.27 mm, a machine direction strength of 1180 g/in, a cross direction strength of 560 g/in, and a wet burst of about 200 g. It contains a wet strength agent and a dry strength agent.

Paper Tissue Example 3

An aqueous slurry of Northern Softwood Kraft (NSK) of about 3% consistency is made up using a conventional pulper and is passed through a stock pipe toward the headbox of the Fourdrinier. A 1% dispersion of Hercules' Kymene 557 LX is prepared and is added to the NSK stock pipe at a rate sufficient to deliver about 0.8% Kymene 557 LX based on the dry weight of the ultimate sanitary tissue paper. The absorption of the permanent wet strength resin is enhanced by passing the treated slurry through an in-line mixer. An aqueous solution of Carboxymethyl cellulose (CMC) dissolved in water and diluted to a solution strength of 1% is added next to the NSK stock pipe after the in-line mixer at a rate of about 0.1% CMC by weight based on the dry weight of the ultimate sanitary tissue paper. The aqueous slurry of NSK fibers passes through a centrifugal stock pump to aid in distributing the CMC. An aqueous dispersion of DiTallow DiMethyl Ammonium Methyl Sulfate (DTDMAMS) (170° F.) at a concentration of 1% by weight is added to the NSK stock pipe at a rate of about 0.1% by weight DTDMAMS based on the dry weight of the ultimate sanitary tissue paper. An aqueous slurry of eucalyptus bleached kraft fibrous pulp fibers (from Aracruz-Brazil) of about 1.5% by weight is made up using a conventional repulper and is passed through a stock pipe toward the headbox of the Fourdrinier. This Eucalyptus furnish joins the NSK slurry at the fan pump where both are diluted with white water to about 0.2% consistency. An aqueous slurry of eucalyptus bleached kraft fibrous pulp fibers (from Aracruz-Brazil) of about 3% by weight is made up using a conventional repulper. The Eucalyptus slurry passes to the second fan pump where it is diluted with white water to a consistency of about 0.2%. The slurries of NSK/eucalyptus and eucalyptus are directed into a multi-channeled headbox suitably equipped with layering leaves to maintain the streams as separate layers until discharged onto a traveling Fourdrinier wire. A three-chambered headbox is used. The eucalyptus slurry containing 48% of the dry weight of the ultimate sanitary tissue paper is directed to the chamber leading to the layer in contact with the wire, while the NSK/eucalyptus slurry comprising 52% (27-35% NSK and 17-25% eucalyptus) of the dry weight of the ultimate paper is directed to the chamber leading to the center and inside layer. The NSK/eucalyptus and eucalyptus slurries are combined at the discharge of the headbox into a composite slurry. The composite slurry is discharged onto the traveling Fourdrinier wire and is dewatered assisted by a deflector and vacuum boxes. The embryonic wet web is transferred from the Fourdrinier wire, at a fiber consistency of about 17% by weight at the point of transfer, to a patterned drying fabric. The drying fabric is designed to yield a pattern-densified tissue with discontinuous low-density deflected areas arranged within a continuous network of high density (knuckle) areas. This drying fabric is formed by casting an impervious resin surface onto a fiber mesh supporting fabric. The supporting fabric is a 48×52 filament, dual layer mesh. The thickness of the resin cast is about 8 mil above the supporting fabric. The knuckle area is about 35-50% and the open cells remain at a frequency of about 68-562 per square inch. Further de-watering is accomplished by vacuum assisted drainage until the web has a fiber consistency of about 23-27%. While remaining in contact with the patterned forming fabric, the patterned web is pre-dried by air blown through to a fiber consistency of about 60% by weight. The semi-dry web is then adhered to the surface of a Yankee dryer with a sprayed creping adhesive comprising a 0.250% aqueous solution of polyvinyl alcohol. The creping adhesive is delivered to the Yankee surface at a rate of 0.1% adhesive solids based on the dry weight of the web. The fiber consistency is increased to about 98% before the web is dry creped from the Yankee with a doctor blade. After the doctor blade, the web is calendared across all its width with a steel to rubber calendar roll operating at a loading of 300-500 psi. The resulting tissue has a basis weight of about 20-25 g/m2; a 1-ply total dry tensile between 250 and 370 g/in, a 1-ply wet burst between 35 and 65 gr/in and a 2-ply caliper of about 0.015-0.020 inches. The resulting tissue is then combined with a like sheet to form a two-ply, creped, pattern-densified tissue so that the eucalyptus fibers face the outside and it is subjected to calendaring between two smooth steel calendar rolls. The product is then ply-bonded using a mechanical plybond wheel to ensure that both plies stay together. The resulting two-ply tissue has a) a total basis weight of about 39-50 g/m2; b) a 2-ply total dry tensile between 450 and 700 gr/in; c) a 2-ply wet burst between 100 and 130 g/in; d) a 4-ply caliper of about 0.51 and 0.89 mm.

The tissue papers described above can be used in combination with any of the lotion described.

Equipment:

A commercially available rotary spray application system RFT-Compact-III with applicator heads for the tissue and textile industry (available from Weitmann&Konrad GmbH & Co KG, Leinfelden Echterdingen, Germany) was modified to be used to practice the present invention. The application head is equipped with 5 sets of rotary disks (type 1/1) and has an effective application width of 448 mm. The housing of the application head was replaced with water heated walls on the top, the bottom and the rear side of the application head. The whole unit was then insulated towards the outside. Two of these modified application heads were used, installed facing each other so that both sides of a tissue web can be treated simultaneously. Heating units with an integrated pump (Type W60/10-12/40, available from Kelviplast GmbH, Germany) are used to supply the application units with water of the desired temperature. In particular, the design of the heating elements was chosen so that the temperature inside the application head is relatively uniform. The lotion infeed of the application heads are connected through a heat traced piping system to a heated pump that is connected through heat traced piping to a heated 100l tank that holds the melted lotion. The return lines of the applicator feed back into the heated tank. A heated flow meter was installed in the lotion supply line between pump and application heads. The flow meter (Promass 63M, available from Endress & Hauser, Switzerland) was connected to the control unit of the RFT-Compact-III system that was then used to control the lotion pump (Gear pump of type Labu Brox) to deliver the desired lotion flow to the application heads.

No changes were made to the setup, shape and dimensions of the rotating surfaces in the commercially available application head. Each set of rotating surfaces consisted of 2 rotating discs stacked on top of each other. The lotion supply to the two rotating surfaces of each stack is equally split. The discs have a diameter of about 98 mm. The five individual stacks of rotating surfaces are spaced apart by about 112 mm. The first, third and fifth set of rotating surfaces is installed vertically shifted versus the second and fourth stack of rotating surfaces to avoid interference between the horizontally overlapping streams of droplets. The sets of rotating surfaces are commercially available from Weitmann & Konrad GmbH & Co, Germany (type 1/1, Art. No. 618996 [upper set] and 618997 [lower set]) The applicator is operated horizontally and with a distance of about 154 mm between the web and the center of the disks. The web is run vertically from top to bottom between the two application heads. Controlled by the windows in the housing between the rotating surfaces and the web, each stack of rotating surfaces covers a cross direction width of about 224 mm on the web with the exception of the two outer stacks of rotating surfaces of the applicator which only cover 112 mm each. At each position the streams of two stacks of rotating surfaces are overlapping. Even distribution to the individual stacks of discs was achieved with throttles of 1 mm diameter, installed between the infeeds to the rotary discs and the central supply pipe of the applicator. The lotion temperature is controlled to a determined value through the heating of the tank, the piping and the temperature in the application heads to the desired value. The flow rate is adjusted to achieve the desired add-on level of the tissue paper. During application, the tissue web is typically kept at room temperature. Some samples were made where the tissue paper was cooled or heated prior to application of the lotion. The lotion almost instantaneously solidifies after impacting the paper web. The application equipment is installed in the converting process after the calendering and high pressure embossing and before the web is cut and folded.

Process Conditions:

The rotating surfaces were operated at 2500 rpm for the samples described below but additional samples have also been made at speeds between 200 rpm and 5000 rpm.

The lotion is usually maintained at a temperature of about 2-10° C. above the melting point, for the lotions described below all temperature settings were kept at 56° C. Products have also been made at temperatures less than 2° C. below and more than 10° C. above the melting point. The web speed for the examples below is 200 m/min, but samples have been also made at web speeds between 10 m/min and 400 m/min.

Data:

Table 1 summarizes the results obtained with the formulations exemplified:

TABLE 1

|  | Formulation 1 | Formulation 3 | Kleenex Balsam |
|---|---|---|---|
| Composition | See lotion example 1<br>40% Stearyl alcohol<br>30% Petrolatum<br>30% Mineral oil | See lotion example 3<br>75% SEFOSE 1618S<br>25% Stearyl alcohol |  |
| Lotion basis weight of the sample | 3.0 g/sqm | 2.1 g/sqm | 3.15 g/sqm (by extraction) |
| Mean basis weight of the deposits | 22.7 g/sqm | 17.2 g/sqm | 12.0 g/sqm |
| $R_2$ | 0.53 | 0.44 | 0.011 |
| $R_3$ | 7.6 | 7.7 | 1.2 |
| $R_4$ | 0.15 | 0.18 | 0.55 |
| R | 0.05 | 0.08 | 0.17 |
| Illustration | — | See FIG. 1a | See FIG. 1b |

Description of FIG. 1a:

Grey value map representing the local basis weight distribution in a 5 mm by 5 mm sample of tissue treated with lotion formulation 3 (left, white represents the maximum level of local lotion basis weight in the sample) and lotion distribution of a cross section of that sample (right, the dashed line in the left picture describes the plane of the cross section).

Description of FIG. 1b:

Grey value map representing the local basis weight distribution in a 5 mm by 5 mm sample of Kleenex Balsam® (left, white represents the maximum level of local lotion basis weight in the sample) and lotion distribution of a cross section of that sample (right).

Test Methods:

Size of the Droplets:

The size droplet size distribution can be measured with a HELOS-VARIO/KF MAGIC laser diffraction system, available from Sympatec GmbH, Germany. Droplet volume can be calculated from the droplet diameter which can be measured by particle size analysis as described below. A relatively large proportion of droplets means at least more than 20%, preferably more than 50% even more preferably more than 70% and most preferably more than 90% of the droplets by weight.

Average Lotion Add-on Level by Solvent Extraction (basis weight of lotion on the tissue): A representative sample of about 2 g of the lotion treated tissue is extracted by Accellerated Solvent Extraction (ASE) using a model ASE 200, available from Dionex Corp., USA. The following conditions are used: 11 ml extraction cell, solvent mixture: 50% Acetone/n-Hexane; temperature: 100° C. (heat and static 5 minutes); pressure: 1000 PSI; two cycles with 100% flush. The solvent is evaporated and the residue is determined gravimetrically. The lotion add on is then calculated as Average lotion=Weight of the extract in [g]×Basis weight of the sample in [g/sqm] add on in g/sqm Weight of the sample before extraction in [g]

While the specified solvent is a preferred choice it may not be suitable to extract all possible lotions that can be thought of. In cases where the lotion is insufficiently soluble in this solvent to perform a quantitative extraction, an alternative solvent has to be chosen that is suitable to quantitatively extract the lotion.

Overall Method for Quantifying the Lotion in Local Area of Deposits:

Determination of local lotion basis weight (LLBW), lotion basis weight of the sample (LBWS), lotion basis weight of the deposits (LBWD), Area affected by deposits (AAD), Area affected by lotion (AAL), and average deposit size (ADS).

The local lotion basis weight is determined by scanning IR/NIR spectroscopy in transmission mode (absorption spectroscopy) using a Perkin Elmer Spectrum Spotlight 300 instrument in combination with Spotlight software version 1.1.0 B38.

The following procedure is applicable to lotions containing linear hydrocarbon components of repeated —(CH2)-units. If the lotion is composed mostly or entirely of other materials, a similar procedure can be applied as described below.

The measurements have to be done with a set of samples representative for the tissue. Each sample is processed as follows: A 5×5 mm sample (or larger) is placed on the sample holder which is mounted on a XY table and the spectral area used for analysis is scanned at a spatial resolution of 25 μm in both x and y dimension. For the analysis of materials containing linear chains of —CH2-groups the region between 4000 cm-1 and 4500 cm-1 is scanned and the range between 4296 cm-1 (W1) and 4368 cm-1 (W2) is used for analysis. At least 16 scans are taken at a resolution of 1 cm-1. If more than 16 scans are used, care needs to be taken that the sample does not change structure as a result of heating up. Next, a map of the local basis weight of the sample is generated. The integrated absorption between W2 and W1 and above a sloping linear baseline is determined for each pixel of 25 μm×25 μm using the ChemiMap menu of the software. The baseline is defined by the absorbency at W1 and W2. The two base points option is chosen in the ChemiMap menu of the software and set at W1 and W2. Start and end point of the integration are also set at W1 and W2. The scaling factor is set to a value V1 which is defined as: V1=F*DW where F is the factor described below and DW=W2-W1 is the delta in wavenumbers between the upper (W2) and the lower (W1) wavenumber in cm$^{-1}$.

The scaling with the factor DW transforms the average absorbance above the baseline within the wavenumber range W1 to W2 into an integrated absorption above the baseline. The factor F translates the integrated absorption into local basis weight in g/sqm.

The file that is generated with the ChemiMap command contains the local basis weight for each pixel of 25 μm×25 μm in area. The file is saved as a text file (.txt format) and also as a bitmap (.bmp format) in 8 bit grey scale format. The .txt file is imported into EXCEL and the first row and first column are removed (they do not contain image data, but position data). The resulting data are representing the array of pixels of local basis weight in g/sqm. The maximum (MaxLBW) and minimum (MinLBW) value, as well as the average (AvgLBW) of the whole dataset is calculated in EXCEL.

The bitmap file (.bmp file) is imported into AnalySIS image analysis software for further processing (Analysis Pro version 3.1 (build508), available from Soft Imaging GmbH, Germany). The imported grey scale file is still in RGB format with all three color channels set equal (in 8 bit resolution). In AnalySIS the file is color separated to extract one of the three identical color channels (red). The resulting file is now scaled from G=0 to G=255, G=0 representing the minimum value (MinLBW) of the original spotlight data and 255 representing the maximum value (MaxLBW) of the original spotlight data. The image is calibrated in x-y by setting the pixel size in x and y dimension to match the original sample. The image is rescaled in z-direction to display the local basis weight values in g/sqm but all calculations within AnalySIS have to be made in the G=0 to G=255 scale. An example of the representation of the sample as a local lotion basis weight map is given in FIGS. 1a and 1b.

The G values can be easily transformed into local lotion basis weight numbers by the following relationship:

$$LLBW = A*(G+\text{OFFSET}), \text{where } A=(\text{Max}LBW-\text{Min}LBW)/255 \text{ and OFFSET}=(255*\text{Min}LBW)/(\text{Max}LBW-\text{Min}LBW)$$

The G values can be easily transformed into local lotion basis weight numbers (LLBW) by the following relationship: G=(LLBW/A)−OFFSET Calculation of the lotion basis weight of the deposits: The average value of all local lotion basis weight datapoints above 10 g/sqm can be calculated from the EXCEL datafile.

The area of tissue affected by lotion is calculated in Analysis by setting a lower threshold at the G value equivalent to 3 g/sqm and calculating the area above that threshold. The setting "holes not filled" is used. The area of the deposits is similarly determined by setting the threshold at a G value equivalent to 10 g/sqm (10 g/sqm equals G=10/A−OFFSET).

If deposits are defined to have a certain minimum and/maximum area is set as a filter. The area percentage of deposits larger than a certain area is calculated by dividing the area of the deposits calculated without area filter, divided by the area of the deposits calculated with area filter.

The factor F to convert integrated absorption values into local lotion basis weight values is determined by the following procedure: A representative set of calibration samples of known average lotion basis weight is scanned in the spectral range used for the analysis as described above and analyzed for integrated peak area between W1 and W2 (4296 cm-1 and 4368 cm-1 for mostly hydrocarbon like materials). The integrated peak area is obtained from the procedure above if the factor F is set equal to 1. The dataset is then imported to EXCEL and the average pixel value of this dataset is calculated. As the factor F was set equal to 1 this value is equal to the mean integrated peak area (AIPA) of the sample in the wave number range W1 to W2. The factor F is then calculated as F=1/slope of a linear least square fit through the origin of the plot of AIPA vs. average lotion basis weight of the sample. Calibration samples to determine the factor F can either be prepared or an existing lotioned sample can be used. If an existing sample is used the lotion basis weight can be determined by extraction. An example for such a procedure is given below. Examples for how the factor F is determined by analyzing an existing sample (market product) and by preparing calibration samples is also given below. It is important, that the absorbency in the wavelength range used for analysis should never exceed about 1 to ensure a linear correlation between the infrared signal and the local lotion basis weight Determination of Factor F By Preparing Calibration Samples (Product of Lotion Example 1):

Preparation of calibration samples: A suitable piece of the substrate of known area, weight and basis weight is evenly treated with lotion, preferably by evenly spraying the molten lotion onto the tissue. A suitable type of equipment is a hot wax cartridge spray gun type MK-DUO Line Art. No. 140101, available from MK Heißwachstechnik GmbH, Aichach, Germany. After the application, the lotion is equilibrated in the sheet by placing the sample in an oven at a temperature of about 10° C. above the mp (or at a temperature suitable to allow for sufficient equilibration of the lotion in the sheet). For relatively low viscosity samples equilibration for about an hour is sufficient. The sample is then cooled down to room temperature and equilibrated for moisture content at 23° C. (+−1° C.) and 50% (+−2%) rel humidity and weighed again. The lotion basis weight of that sample [in g/sqm] is then calculated as (sample weight after lotion treatment [in grams]−sample weight before lotion treatment [in grams])

divided by area of the sample [in sqm]. The samples are then analyzed by the procedure described above to determine the factor F. Preferably, calibration samples are prepared in a range of lotion basis weights that include the range to be measured.

Calibration samples should be used to confirm linearity within the calibration range: The calibration curve shown as FIG. 2 was generated for the lotion of lotion example 1. Determination of Factor F for a market product (Kleenex Balsams, sold in Germany by Kimberly Clark): The basis weight of the sample is determined by a standard procedure. The sample is then analyzed by the procedure described above for the average integrated peak area between 4296 cm-1 and 4368 cm-1. The sample is then extracted by the procedure described below to determine the lotion add-on. The Factor F is then calculated as Factor $F$=lotion basis weight [g/sqm]/average integrated peak area If the lotion does not contain a sufficient amount of linear hydrocarbon like material, or the substrate contains materials that do not allow for a quantification of lotion between 4296 cm-1 and 4368 cm-1, a different wavenumber range in the infrared or near infrared range has to be identified that is suitable to quantify the lotion by IR spectroscopy. Any wavenumber range with a linear correlation between integrated absorption coefficient above base line and lotion basis weight can be used. If more than one possible wavenumber range can be identified, the range with the best signal to noise ratio is used. Whenever the lotion is based on linear hydrocarbon like materials with CH2 groups the absorption band between 4296 cm-1 and 4368 cm-1 should be used.

All documents cited herein are, in their relevant part, incorporated herein by reference; the citation of any document is not to be construed as an admission that it takes away patentability of the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A paper tissue having first and second opposed surfaces, comprising a lotion comprising an immobilizing agent, a transferable agent, and an emollient on the first surface of said paper tissue, said lotion being present in substantially discrete deposits on said first surface and covering larger than 70% of the total area of the first surface, and wherein said deposits have an average basis weight of from 11 g/sqm to 22.7 g/sqm.

2. The paper tissue of claim 1 wherein the basis weight of said lotion on said tissue is equal or less than 9 g/sqm.

3. The paper tissue of claim 1, wherein a ratio $R_3$ is defined as $$R_3 = \frac{\text{lotion basis weight of said deposits (in g/}sqm\text{)}}{\text{lotion basis weight of said tissue (in g/}sqm\text{)}}$$

and said ratio $R_3$ is at least 5.

4. The paper tissue of claim 1, wherein a ratio $R_1$ is defined as $$R_1 = \frac{\text{Area of said portions affected by said lotion (in }sqcm\text{)}}{\text{Total area of said tissue (in }sqcm\text{)} \times \text{said lotion basis weight of said tissue (in g/}sqm\text{)}}$$

and in that said ratio $R_1$ is less than 0.15 sqm/g.

5. The paper tissue of claim 2, wherein ratio $R_2$ is defined as $$R_2 = \frac{\text{lotion basis weight of said deposits (in g/}sqm\text{)} * \text{area of said deposits (}sqm\text{)}}{\text{lotion basis weight of said tissue (in g/}sqm\text{)} * \text{total area of said tissue (}sqm\text{)}}$$

and said ratio $R_2$ at least 0.02.

6. The paper tissue of claim 1 wherein 20% or more of the area affected by deposits is covered with deposits larger than 0.005 sqmm.

7. A paper tissue product comprising the tissue of claim 1 wherein said paper tissue product is a multiply tissue product of at least 2 plies having 2 external surfaces and at least 2 internal surfaces and wherein any of said external surfaces has more lotion than its corresponding internal surface.

8. A paper tissue product comprising the tissue of claim 1 wherein said paper tissue product is a multiply tissue of at least 3 plies having at least one 1 internal ply and 2 external plies and wherein said external plies taken together comprise 60% (by weight) or more of the total amount of lotion of said paper tissues product.

9. The paper tissue of claim 1 wherein said lotion basis weight on said tissue is at least 0.3 g/sqm.

10. The paper tissue of claim 1 wherein said lotion comprises at least 30% (w/w) of stearyl alcohol, at least 20% (w/w) of petrolatum and at least 10% (w/w) of mineral oil.

11. The paper tissue of claim 1 wherein said lotion comprises at least 50% (w/w) of a sucrose ester of a fatty acid and at least 10% (w/w) of stearyl alcohol.

12. The paper tissue of claim 1 wherein said lotion comprises between 0.01% (w/w) and 5% (w/w) of 2-isopropyl-N,2,3 trimethylbutyramide.

* * * * *